United States Patent
Handin et al.

(10) Patent No.: US 6,605,277 B2
(45) Date of Patent: Aug. 12, 2003

(54) CONFORMATION-SPECIFIC ANTI-VON WILLEBRAND FACTOR ANTIBODIES

(75) Inventors: Robert I. Handin, Needham, MA (US); Huabing Yuan, Chesterfield, MO (US); Anne McLeod, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 25 days.

(21) Appl. No.: 09/823,748

(22) Filed: Apr. 6, 2001

(65) Prior Publication Data

US 2001/0024647 A1 Sep. 27, 2001

Related U.S. Application Data

(62) Division of application No. 09/421,045, filed on Oct. 20, 1999, now Pat. No. 6,251,393.
(60) Provisional application No. 60/105,389, filed on Oct. 23, 1998.

(51) Int. Cl.$^7$ .............................................. A61K 39/395
(52) U.S. Cl. ................................. 424/135.1; 424/145.1
(58) Field of Search .......................... 424/135.1, 145.1; 530/387.1, 387.3, 388.25, 389.3, 387.9

(56) References Cited

U.S. PATENT DOCUMENTS

| | | | |
|---|---|---|---|
| 5,114,842 A | | 5/1992 | Plow et al. |
| 5,336,618 A | | 8/1994 | Coller |
| 5,493,007 A | | 2/1996 | Burnier et al. |
| 5,688,912 A | | 11/1997 | Dadd et al. |
| 5,804,159 A | | 9/1998 | Eibl et al. |
| 5,916,805 A | * | 6/1999 | Nagano et al. |

FOREIGN PATENT DOCUMENTS

| | | |
|---|---|---|
| EP | 319 315 | 6/1989 |
| EP | 795 608 | 9/1997 |
| WO | WO 93/16712 | 9/1993 |

OTHER PUBLICATIONS

Huston et al PNAS (1988) 85:5879–83.*
Adams, et al., "Development of Potent Agonist Antibodies to c–Mpl from a Human scFv Phage Display Library," *Blood* 90(10):55A (1995), abstract XP002095743.
Bird, et al., "Single–Chain Antigen–Binding Proteins," *Science* 242:423–426 (1988).
de Kruif, et al., "Selection and Application of Human Single Chain Fv Antibody Fragments from a Semi–Synthetic Phage Antibody Display Library with Designed CDR3 Regions," *J. Mol. Biol.* 248: 97–105 (1995).
Hoylaerts, "Platelet–Vessel Wall Interactions in Thrombosis and Restenosis Role of von Willebrand Factor," *Verhandelingen—Koninklijke Academie Voor Geneeskunde Van Belgie* 59(3):161–183 (1997).
Huston, et al., "Protein Engineering of Antibody Binding Sites: Recovery of Specific Activity in an Anti–Digoxin Single–Chain Fv Analogue Produced in *Escherichia coli*," *Proc. Natl. Acad. Sci. USA* 85:5879–5833 (1988).
Lafaye, et al., "Biologically Active Human Anti–Crotoxin scFv Isolated from a Semi–Synthetic Phage Library," *Immunotechnology* 3:117–125 (1997).
McLeod, et al., "Identification of a Conformation–Specific Antibody to the vWF–A1 Domain by Repertoire Cloning," *Blood* 92(10)(Supp. 1)(Part 1–2):501A (1998), Meeting Info: 40$^{th}$ Annual Meeting of the American Society of Hematology, Miami Beach, FL, Dec. 4–8, 1998, abstract XP000876694.
Vaughn, et al., "Human Antibodies with Sub–Nanomolar Affinities Isolated from a Large Non–Immunized Phage Display Library," *Nature Biotechnology* 14:309–314 (1996).
Yamamoto, et al., "Antagonism of vWF Inhibits Both Injury Induced Arterial and Venous Thrombosis in the Hamster," *Thromb. Haemost.* 79(1):202–210 (1998).
Yuan, et al., "A Structural and Functional Study of the von Willebrand Factor A1 Domain Using A1 and A3 Domain Specific Antibodies," *Blood* 86(10)(Supp. 1):70A (1995), Meeting Info: 37$^{th}$ Annual Meeting of the American Society of Hematology, Seattle, WA, Dec. 1–5, 1995, abstract XP000876716.

* cited by examiner

*Primary Examiner*—Patrick J. Nolan
*Assistant Examiner*—Amy DeCloux
(74) *Attorney, Agent, or Firm*—Michael A. Sanzo; Fitch, Even, Tabin & Flannery

(57) ABSTRACT

The present invention is directed to antibodies and antibody fragments that bind specifically to the active conformation of human von Willebrand factor. Most preferred are recombinantly produced single chain variable immunoglobulin fragments. Because the antibodies or antibody fragments act only at the sites of thrombus formation and do not interfere with the normal activity of circulating platelets, they are particularly well suited for use as antithrombotic agents in a wide variety of applications.

6 Claims, No Drawings

CONFORMATION-SPECIFIC ANTI-VON WILLEBRAND FACTOR ANTIBODIES

CROSS REFERENCE TO RELATED APPLICATIONS

The present application is a division of U.S. application Ser. No. 09/421,045, filed Oct. 20, 1999 now U.S. Pat. No. 6,251,393, U.S. Ser. No. 09/421,045 claims the benefit of U.S. provisional application No. 60/105,389, filed on Oct. 23, 1998 (now abandoned).

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to compositions containing one or more agents that recognize the active conformation of human von Willebrand and that inhibit the interaction between this factor and platelets. The compositions can be used either therapeutically or prophylactically to prevent thrombus formation in patients. Compositions may also be used diagnostically to detect sites where thrombosis is likely to occur.

BACKGROUND OF THE INVENTION

Thrombosis occurring at atherosclerotic plaques is a major cause of morbidity and mortality in the United States. The initial event in thrombus formation is the adhesion of platelets to an injured or diseased arterial wall. Adhesion is enhanced and stabilized by a plasma protein, the von Willebrand Factor, which forms a bridge between components of the vessel wall and receptors on the platelet surface, primarily the glycoprotein Ib/IX/V complex. There are two unique features of this interaction that set it apart from adhesive events involving other cells and plasma proteins. First, the interaction of vWF with platelets is the only reaction that permits platelets to remain attached to vessel walls under the high shear/high flow conditions present in arteries, arterioles, and capillaries. Second, vWF is the only plasma adhesive protein which must undergo a conformation change before it is able to bind to its platelet receptor.

Attempts have been made to prevent thrombus formation by introducing either antibodies (see, e.g., EP 747,060; WO 96/17078; and U.S. Pat. No. 5,336,618) or peptides (see, e.g., U.S. Pat. No. 5,688,912; U.S. Pat. No. 5,493,007; U.S. Pat. No. 5,114,842; WO 93/16712; and EP 319,315) that bind to platelet receptors. One problem with the use of such agents is that they are nonselective—interfering with the function of all circulating platelets. The development of an agent that acts specifically at sites of thrombosis to inhibit platelet adhesion would represent a clear advance in the treatment and prevention of stroke, myocardial infarction, and related conditions. Equally important, such an agent might be used diagnostically to identify sites where blood vessels are at risk of becoming occluded.

SUMMARY OF THE INVENTION

Using recombinant DNA and phage display technology, murine anti-human vWF antibodies have been made which specifically recognize activated vWF and interfere with its ability to promote platelet adhesion. The antibodies act at sites of thrombus formation but do not bind to circulating, unactivated forms of vWF. This results in antithrombotic agents that are both safer and more efficacious.

In its first aspect, the invention is directed to a composition comprising an antibody that binds selectively to the active conformation of human vWF, thereby inhibiting its ability to interact with platelets. As used herein, "selective binding" means that an antibody has at least a tenfold, and preferably at least a hundredfold, greater affinity for vWF when it is in its active conformation compared to when it is unactivated. Relative affinity can be determined using standard binding assays in which vWF is examined both in the presence and absence of an activating agent such as Ristocetin. Unless otherwise indicated, the term "antibody" refers both to intact antibodies as well as to fragments, particularly to recombinantly engineered fragments, that retain their ability to bind to antigen. Inhibition of platelet binding occurs whenever there is a statistically significant reduction in the amount of vWF-induced platelet aggregation in the presence of antibody. In the most preferred embodiment, compositions contain recombinantly produced single chain variable region (ScFv) fragments of immunoglobulins directed against a vWF-A1 epitope. Typically, the ScFv fragment will be derived from the mouse and compositions designed for therapeutic administration will contain a pharmaceutically acceptable carrier.

In a second aspect, the invention is directed to a method of identifying an ScFv fragment that binds selectively to the active conformation of human vWF. The method involves immunizing an animal, preferably a mouse, with an immunogen (either a peptide or a nucleic acid encoding a peptide) derived from the A1 region of human vWF. After immunization, mRNA is isolated from the animal and used to produce an ScFv cDNA library in a bacteriophage capable of displaying the fragments. The library is then screened to identify phage expressing a fragment that binds selectively to the active conformation of vWF. Binding may be determined directly, in the presence and absence of an agent inducing vWF to assume an active conformation, or by examining the inhibition of vWF-induced platelet aggregation. Once an appropriate phage has been identified, the DNA encoding the ScFv fragment may be recovered and subcloned in an expression vector. Finally, recombinant ScFv is produced in a host cell transformed with the vector and purified. The ScFv fragments obtained in this manner are part of the invention.

The present invention is also directed to a method for preventing thrombus formation in a patient by administering a pharmaceutical composition containing an antibody of the type discussed above, i.e., an antibody binding selectively to the active conformation of human vWF. The pharmaceutical composition should be administered at a dosage sufficient to prevent the binding of activated vWF to platelets and may be administered either therapeutically or prophylactically. Therapeutically, the composition may be administered to a patient with an occluded blood vessel either alone or in conjunction with thrombolytic agents such as tissue plasminogen activator or streptokinase. Prophylactically, the compositon may be administered to patients at risk of thrombosis due to atherosclerosis or during medical procedures that carry a risk of vessel occlusion, e.g., angioplasty, stent placement, or graft insertion.

Antibodies may also be detectably labeled and used in conjunction with imaging techniques to determine sites within the vasculature where thrombosis is likely to occur, e.g., where there has been plaque rupture or blood vessel damage. Because ScFv fragments are missing regions of antibodies that are often responsible for nonspecific binding, these fragments are preferred for all in vivo diagnostic procedures.

DETAILED DESCRIPTION OF THE INVENTION

The present invention is directed to antibodies that specifically recognize the activated conformation of vWF and prevent it from interacting with platelets. It encompasses methods for making ScFv conformation-specific fragments and methods for using such antibodies diagnostically, therapeutically and prophylactically.

A. Antibodies Selectively Binding to the Active Conformation of vWF

Methods for making and detecting antibodies have been described in numerous standard reference works such as: Harlow et al., *Antibodies, A Laboratory Manual*, Cold Spring Harbor Laboratory, N.Y. (1988); Klein, *Immunology: The Science of Self-Nonself Discrimination* (1982); Kennett et al., *Monoclonal Antibodies and Hybridomas: A New Dimension in Biological Analyses* (1980); and Campbell, "Monoclonal Antibody Technology," in *Laboratory Techniques in Biochemistry and Molecular Biology* (1984). The process for producing conformation-specific antibodies may involve either injecting the intact vWF protein into an appropriate animal or, preferably, injecting short peptides made to correspond to regions of vWF that are believed to interact with platelets, i.e., peptides from the A1 domain. As an alternative, nucleic acids encoding vWF or portions of vWF may be administered to animals (see, U.S. Pat. No. 5,589,466; U.S. Pat. No. 5,580,859; and U.S. Pat. No. 5,703,055). The preferred animal for immunization is the mouse.

The term "antibody" refers to monoclonal antibodies, polyclonal antibodies and to fragments of these antibodies that continue to bind to antigen. Polyclonal antibodies are derived from the sera of animals immunized with the antigen. Monoclonal antibodies can be prepared using hybridoma technology (Kohler et al., *Nature* 256:495 (1975); Hammerling et al., in *Monoclonal Antibodies and T-Cell Hybridomas*, Elsevier, N.Y. pp. 563–681 (1981)). In general, this technology involves immunizing an animal (usually a mouse) with antigen, extracting splenocytes from the immunized animal and then fusing the splenocytes with myeloma cells, e.g., $SP_2O$ cells. After fusion, the resulting hybridoma cells are selectively maintained in HAT medium and then cloned by limiting dilution (Wands et al., *Gastroenterology* 80:225–232 (1981)). The cells obtained through such selection are then assayed to identify clones which secrete antibodies capable of binding specifically to the active conformation of vWF. Antigen-binding fragments may be produced by proteolytically cleaving intact antibodies using enzymes such as papain (to produce Fab fragments) or pepsin (to produced $F(ab')_2$ fragments).

Assays appropriate for measuring the binding of antibody to vWF are well known in the art. For example, radioimmunoassays or immunometric assays, also known as "two-site" or "sandwich" assays, may be used (see Chard; "An Introduction to Radioimmune Assay and Related Techniques," in *Laboratory Techniques in Biochemistry and Molecular Biology*, North Holland Publishing Co., N.Y. (1978)). In one variety of such assays, the antibody to be tested is immobilized on a solid support and then incubated with a solution containing detectably labeled vWF in the presence and absence of an activator such as Ristocetin. Nonspecific binding may be determined by carrying out parallel incubations in the presence of an excess quantity of unlabeled vWF and activator. This should be subtracted from total binding, i.e., binding in the absence of unlabeled vWF, to arrive at the specific binding for each sample tested. Other steps such as washing, stirring, shaking, filtering, and the like may be included in the assays as necessary. Typically, wash steps are included after the separation of bound ligand from ligand remaining in solution and prior to the quantitation of binding, e.g., by counting radioactive isotope. As an alternative, assays examining the ability of antibodies to inhibit the aggregation of platelets in the presence of activated vWF may be used.

It is highly desirable that antibodies identified as binding to the active conformation of vWF be reexamined in a concentration range sufficient to perform a Scatchard analysis on the results. This type of analysis is well known in the art and can be used for determining the affinity of an antibody for an antigen (see, e.g., Ausubel et al., *Current Protocols in Molecular Biology*, pp. 11.2.1–11.2.19 (1993); *Laboratory Techniques in Biochemistry and Molecular Biology*, Work et al., N.Y. (1978)). Computer programs may be used to help in the analysis of results (see, e.g., Munson, P., *Methods Eenzymol.* 92:543–577 (1983); McPherson, "Kinetic, EBDA Ligand, Lowry—A Collection of Radioligand Binding Analysis Programs," Elsevier-Biosoft, U.K. (19985)).

B. ScFv Fragments

ScFv fragments are proteins consisting of the $V_L$ and $V_H$ antibody polypeptide chains synthesized as a single chain with the carboxyl terminus of $V_L$ linked by a peptide bridge to the amino terminus of $V_H$. Methods for recombinantly producing these peptides in *E. coli* are well known in the art (see Bird et al., *Science* 242:423–426 (1988); Huston et al., *Proc. Nat'l Acad. Sci. USA* 85:5879–5883 (1988); and de Kruif et al., *J. Mol. Biol.* 248:97–105 (1995)). Although any method for generating these fragments is compatible with the present invention, the preferred method consists of immunizing mice with peptides derived from the A1 region of vWF. After immunization, splenic mRNA is harvested from the mice and used to produce a cDNA library in a bacteriophage which displays the ScFv fragments. Phage are then screened to determine those that interact specifically with the activated form of vWF. ScFv segments are recovered from these phage, incorporated into an expression vector, and cloned in *E. coli*. The recombinant ScFv fragments produced by the bacteria may be purified and further tested for binding affinity to both activated and unactivated vWF.

Using this procedure, recombinant antibody fragments have been obtained that have three important characteristics: 1) they only bind to vWF that has been activated by prior immobilization or by exposure to an activating agent like Ristocetin; 2) they inhibit the binding of vWF to platelets as measured using a Ristocetin-induced platelet agglutination assay; and 3) they inhibit flow-dependent platelet adhesion to immobilize vWF. The selectivity of these fragments makes them suitable for use in pharmaceutical compositions designed for administration to patients as antithrombotic agents.

C. Therapeutic and Diagnostic Use of Antibodies

Pharmaceutical compositions containing antibodies specific for the active conformation of vWF may be used to treat or prevent coronary arterial ischemic syndromes, including unstable angina and acute myocardial infarction, as well as to treat cerebrovascular and peripheral vascular ischemia. The compositions may also be used in conjunction with therapeutic interventions such as stent placement, balloon angioplasty, or graft insertion.

Any route of administration and dosage form is compatible with the present invention and conformation-specific antibodies may be administered as either the sole activate agent or in combination with other therapeutically active drugs such as thrombolytics. In general, parenteral delivery using the intravenous, intraarterial, intramuscular, intraperitoneal, intracutaneous, or subcutaneous routes is preferred.

Dosage forms may be prepared using methods that are standard in the art (see, e.g., *Remington's Pharmaceutical Sciences*, 16th ed., A. Oslo ed., Easton, Pa. (1980)). Active agents may be used in combination with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Solutions can be prepared using water or physiologically compatible buffers, or organic solvents such as ethanol, 1,2-propylene glycol, polyglycols, dimethyl sulfoxide, fatty alcohols, triglycerides, partial esters of glycerine, and the like. Preferred parenteral compositions may be prepared using conventional techniques and include sterile isotonic saline, water, 1,3-butanediol, ethanol, 1,2-propylene glycol, polyglycols mixed with water Ringer's solution, etc.

The dosage of active agent to be administered to a patient will be determined using methods well known in the art and will depend upon a wide variety of clinical factors. By way of example, a typical pharmaceutical composition for injection may comprise 1 ml of sterile buffered water and 10 mg of antibody. A typical composition for intravenous infusion may comprise 250 ml of sterile Ringer's solution and 10 mg of protein. The compositions may be administered either prophylactically or therapeutically. In therapeutic applications, compositions are administered to a patient suffering from a disease or condition in an amount sufficient to produce a positive therapeutic effect. For example, in the case of angina, dosage should be adjusted to the point where pain is alleviated. For occluded vessels, it is expected that antibodies will be used in conjunction with one or more thrombolytic agents and dosage should be sufficient to achieve, at least partial, reperfusion.

Prophylactically, pharmaceutical compositions containing the conformation-specific antibodies are administered to a patient in order to prevent the onset of an unwanted disease or condition. Thus, compositions may be administered to a patient with atherosclerotic plaques to prevent thrombosis or to patients undergoing therapeutic procedures such as angioplasty to reduce the chance of vessel occlusion.

Antibodies may also be used diagnostically to identify sites of potential thrombus formation. This may be accomplished by labeling antibodies with an agent that is detectable by imaging techniques such as NMR, MRI, or CAT scans. ScFv fragments should be especially useful in this regard in that the portions of antibodies that are primarily responsible for nonspecific in vivo binding are not present in these molecules.

All references cited herein are fully incorporated by reference. Having now fully described the invention, it will be understood by those of skill in the art that the invention may be performed within a wide and equivalent range of conditions, parameters and the like, without affecting the spirit or scope of the invention or embodiment thereof.

What is claimed is:

1. A method of inhibiting the binding of human vWF to platelets, comprising contacting said human vWF with a single chain variable region immunoglobulin (ScFv) fragment that binds to the active conformation of human vWF with at least a hundredfold greater affinity than to unactivated vWF and that inhibits the binding of vWF to platelets, wherein said ScFv fragment is produced by a method comprising:

(a) immunizing an animal with an immunogen derived from the A1 region of human vWF;
    (b) isolating mRNA from the immunized animal of step (a);
    (c) producing a cDNA library from the isolated mRNA of step (b) in a bacteriophage capable of displaying ScFv fragments encoded by cloned cDNA; and
    (d) screening the library of step (c) to identify a bacteriophage displaying a ScFv fragment that binds selectively to the active conformation of vWF.

2. A method of inhibiting the binding of human vWF to platelets, comprising contacting said human vWF with a single chain variable region immunoglobulin (ScFv) fragment that binds to the active conformation of human vWF with at least a hundredfold greater affinity than to unactivated vWF and that inhibits the binding of vWF to platelets, wherein said ScFv fragment is produced by a method comprising:

(a) immunizing an animal with an immunogen derived from the A1 region of human vWF;
    (b) isolating mRNA from the immunized animal of step (a);
    (c) producing a cDNA library from the isolated mRNA of step (b) in a bacteriophage capable of displaying ScFv fragments encoded by cloned cDNA;
    (d) screening the library of step (c) to identify a bacteriophage displaying a ScFv fragment that binds selectively to the active conformation of vWF;
    (e) subcloning the recombinant DNA encoding the ScFv fragment identified in step (d) in an expression vector;
    (f) transforming a host cell capable of expressing recombinant ScFv with the expression vector of step (e); and
    (g) purifying the recombinant ScFv fragment produced by the host cell of step (f).

3. A method of inhibiting the binding of human vWF to platelets, comprising contacting said human vWF with a single chain variable region immunoglobulin (ScFv) fragment that binds to the active conformation of human vWF with at least a hundredfold greater affinity than to unactivated vWF and that inhibits the binding of vWF to platelets.

4. A method of preventing thrombus formation in a patient, comprising administering to said patient a pharmaceutical composition comprising a single chain variable region immunoglobulin (ScFv) fragment that binds to the active conformation of human vWF with at least a hundredfold greater affinity than to unactivated vWF and that inhibits the binding of vWF to platelets, wherein said ScFv fragment is produced by a method comprising:

(a) immunizing an animal with an immunogen derived from the A1 region of human vWF;
    (b) isolating mRNA from the immunized animal of step (a);
    (c) producing a cDNA library from the isolated mRNA of step (b) in a bacteriophage capable of displaying ScFv fragments encoded by cloned cDNA;
    (d) screening the library of step (c) to identify a bacteriophage displaying a ScFv fragment that binds selectively to the active conformation of vWF; and
    wherein said pharmaceutical composition is administered at a dosage sufficient to inhibit said thrombus formation.

5. A method of preventing thrombus formation in a patient, comprising administering to said patient a pharmaceutical composition comprising a single chain variable region immunoglobulin (ScFv) fragment that binds to the active conformation of human vWF with at least a hundredfold greater affinity than to unactivated vWF and that inhibits the binding of vWF to platelets, wherein said ScFv fragment is produced by a method comprising:

(a) immunizing an animal with an immunogen derived from the A1 region of human vWF;

(b) isolating mRNA from the immunized animal of step (a);

(c) producing a cDNA library from the isolated mRNA of step (b) in a bacteriophage capable of displaying ScFv fragments encoded by cloned cDNA;

(d) screening the library of step (c) to identify a bacteriophage displaying a ScFv fragment that binds selectively to the active conformation of vWF;

(e) subcloning the recombinant DNA encoding the ScFv fragment identified in step (d) in an expression vector;

(f) transforming a host cell capable of expressing recombinant ScFv with the expression vector of step (e);

(g) purifying the recombinant ScFv fragment produced by the host cell of step (f); and wherein said pharmaceutical composition is administered at a dosage sufficient to inhibit said thrombus formation.

6. A method of preventing thrombus formation in a patient comprising administering to said patient a pharmaceutical composition comprising a single chain variable region immunoglobulin (ScFv) fragment that binds to the active conformation of human vWF with at least a hundredfold greater affinity than to unactivated vWF and that inhibits the binding of vWF to platelets, and wherein said pharmaceutical composition is administered at a dosage sufficient to inhibit said thrombus formation.

* * * * *